(12) United States Patent
Mori et al.

(10) Patent No.: US 8,997,349 B2
(45) Date of Patent: Apr. 7, 2015

(54) MANUFACTURING METHOD FOR MEDICAL EQUIPMENT FOR REDUCING PLATELET ADHESION ON A SURFACE IN CONTACT WITH BLOOD

(71) Applicant: Thoratec Corporation, Pleasanton, CA (US)

(72) Inventors: Takehisa Mori, Kanagawa (JP); Atsushi Okawa, Higashikurume (JP); Takeshi Tsubouchi, Kanagawa (JP); Kensuke Uemura, Tsubame (JP)

(73) Assignee: Thoratec Corporation, Pleasanton, CA (US)

( * ) Notice: Subject to any disclaimer, the term of this patent is extended or adjusted under 35 U.S.C. 154(b) by 281 days.

(21) Appl. No.: 13/834,211

(22) Filed: Mar. 15, 2013

(65) Prior Publication Data

US 2013/0230422 A1    Sep. 5, 2013

Related U.S. Application Data

(63) Continuation of application No. PCT/JP2011/071110, filed on Sep. 15, 2011.

(30) Foreign Application Priority Data

Sep. 17, 2010   (JP) ................................ 2010-210173

(51) Int. Cl.
  *A61M 1/10*   (2006.01)
  *A61L 27/06*   (2006.01)
  (Continued)

(52) U.S. Cl.
  CPC ................ *A61M 1/101* (2013.01); *A61L 27/06* (2013.01); *A61L 31/022* (2013.01); *A61L 33/0094* (2013.01); *C22F 1/183* (2013.01)

(58) Field of Classification Search
  CPC ... A61L 27/06; A61L 31/022; A61L 33/0094; A61L 31/00; A61M 1/101; C22F 1/183; C22F 3/00; Y10T 428/2809
  See application file for complete search history.

(56) References Cited

U.S. PATENT DOCUMENTS

2003/0019850 A1*  1/2003  Kensuke et al. ......... 219/121.61
2005/0287022 A1* 12/2005  Yaegashi et al. ............. 417/420
(Continued)

FOREIGN PATENT DOCUMENTS

JP    10-248923 A   9/1998
JP    11-506807 A   6/1999
(Continued)

OTHER PUBLICATIONS

English translation of International Preliminary Report on Patentability issued Apr. 16, 2013 by the International Bureau of WIPO in International Application No. PCT/JP2011/071110 (9 pgs).
(Continued)

*Primary Examiner* — Alexander P Taousakis
(74) *Attorney, Agent, or Firm* — Kilpatrick Townsend & Stockton LLP

(57) ABSTRACT

A manufacturing method for medical equipment involves electron beam irradiating a titanium or titanium alloy substrate surface that has at least been machined, whereby platelet adhesion of the surface to be contacted by blood is reduced. The manufacturing method for medical equipment can also use a specific pre-processing method and an electron beam irradiation method to reduce the platelet adhesion of the surface which is to be contacted with blood, to suppress the formation of minute depressions (craters) in the surface, which can occur due to the irradiation by an electron beam.

19 Claims, 12 Drawing Sheets

(51) Int. Cl.
*A61L 31/02* (2006.01)
*A61L 33/00* (2006.01)
*C22F 1/18* (2006.01)

(56) References Cited

U.S. PATENT DOCUMENTS

| | | | |
|---|---|---|---|
| 2008/0243198 A1* | 10/2008 | Pederson | 607/2 |
| 2010/0221130 A1 | 9/2010 | Yaegashi et al. | |
| 2011/0270182 A1* | 11/2011 | Breznock et al. | 604/122 |
| 2013/0053693 A1* | 2/2013 | Breznock et al. | 600/433 |
| 2013/0053755 A1* | 2/2013 | Kerr | 604/8 |
| 2014/0364391 A1* | 12/2014 | Hai et al. | 514/55 |

FOREIGN PATENT DOCUMENTS

| | | |
|---|---|---|
| JP | 2003-111778 A | 4/2003 |
| JP | 2005-270345 A | 10/2005 |
| JP | 2005-287598 A | 10/2005 |
| JP | 2009-279268 A | 12/2009 |
| JP | 2010-000295 A | 1/2010 |
| JP | 2010-068935 A | 4/2010 |
| WO | 96/40308 A1 | 12/1996 |

OTHER PUBLICATIONS

Lin Z. et al., "Influence of Chemical Composition and Structure on the Blood Compatiblility of Titanium Oxide Films Prepared by E-beam Evaporation", pp. 223-228; ISSN: 0737-5921, 2008 (month unknown).

Y. Uno et al., "High Efficiency Finishing of Biomaterial Titanium Alloy by Wide-area Electron Beam Irradiation" pp. 279-280; ISSN:1348-3943, 2004 (month unknown).

K. Wakabayashi et al., "Surface Modification of Dental Alloy by Electron-Beam System (Part 1)—Change of Surface Roughness",with partial English translation, p. 177, ISSN: 0286-5858, 2004 (month unknown).

J. Tokunaga et al., "Surface Modification of Dental Alloy by Electron-Beam System (Part 4)—Examination on the surface of Titanium and Au—Ag—Pd Alloy", p. 407; USSB: 0286-5858, 2005 (month unknown).

J. Tokunaga et al., "Large-area electron beam irradiation for surface polishing of cast titanium", pp. 571-577; ISSN: 0287-4547, 2009 (month unknown).

A. Okada et al., "New Surface Modification Method of Bio-Titanium Alloy by EB Polishing", pp. 694-700, ISSN:1881-3054, 2008 (month unknown).

M. E. Jones et al., "Protein Adsorption and Platelet Attachment and Activation, on TiN, TiC, and DLC Coatings on Titanium for Cardiovascular Applications", pp. 413-421, ISSN: 0021-9304.

International Search Report dated Nov. 15, 2011, issued in corresponding International Application No. PCT/JP2011/071110. (3 pgs.).

* cited by examiner

R　　D　　SD　　S　　FS

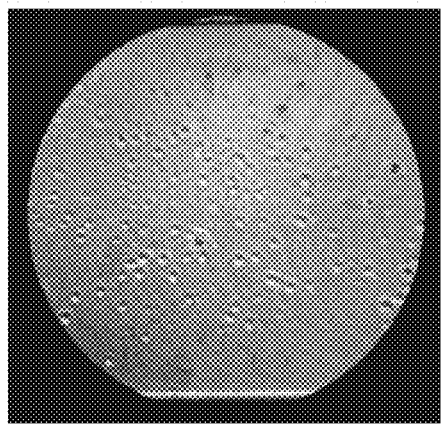 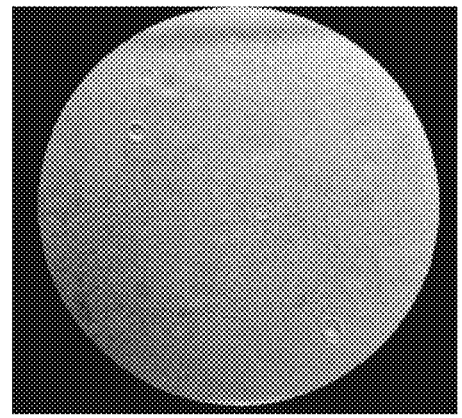
FIG. 14A    FIG. 14B
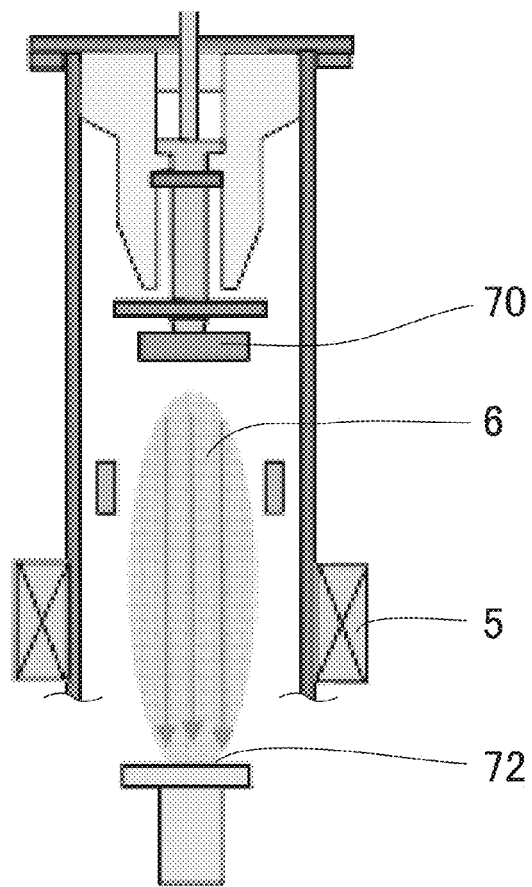
FIG. 15

FIG. 16
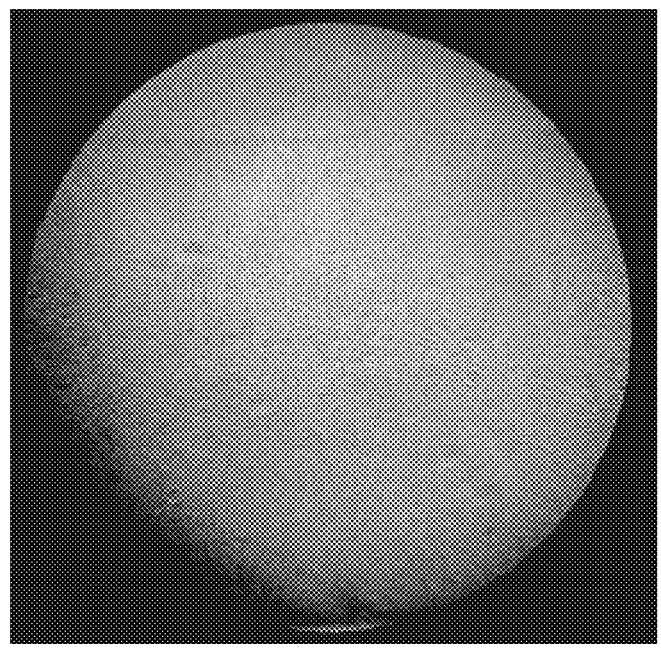
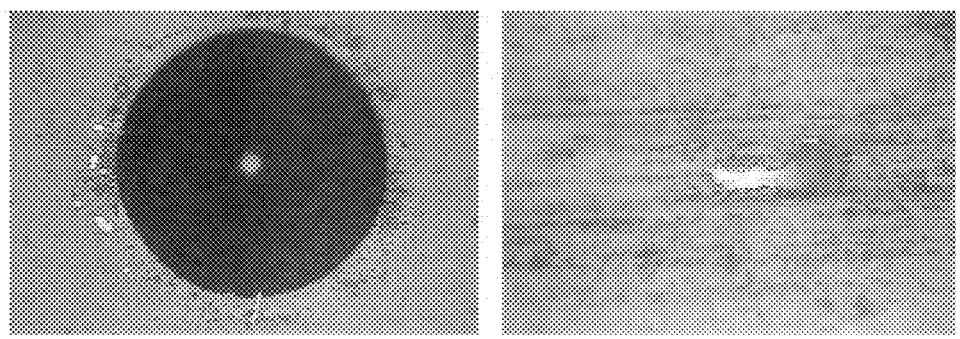
FIG. 17A      FIG. 17B

MANUFACTURING METHOD FOR MEDICAL EQUIPMENT FOR REDUCING PLATELET ADHESION ON A SURFACE IN CONTACT WITH BLOOD

CROSS REFERENCES TO RELATED APPLICATIONS

The present application is a continuation application of International Application No. PCT/JP2011/071110 filed on Sep. 15, 2011, and claims priority to Japanese Patent Application No. 2010-210173 filed on Sep. 17, 2010, the entire content of both of which is incorporated herein by reference.

TECHNICAL FIELD

The present invention generally relates to a method of manufacturing a medical device. More particularly, the invention pertains to a method of manufacturing a medical device in which a surface of the medical device brought into contact with blood has reduced platelet adhesion.

BACKGROUND DISCUSSION

Among titanium or titanium alloy base materials are pure titanium (e.g. JIS Class 1 and 2) and high-strength titanium alloys exemplified by α-β alloys, 6-4 alloys (e.g. JIS Class 60), β alloys, and 15-3-3-3 alloys. Among titanium or titanium alloy base materials used for medical metallic devices are 6-4 alloys and ELI (Extra Low Interstitial Elements) materials that are 6-4 alloys containing oxygen, nitrogen, hydrogen, and iron in particularly reduced amounts. The 6-4 alloys and ELI materials possess a relatively high strength and consistently maintain their high strength even at a high temperature, but are difficult to machine, easily wear, and are liable to develop seizure or galling.

A medical device made of a titanium or titanium alloy base material is manufactured by cutting or otherwise machining a block material, which is produced by, for example, rolling, into a given shape.

Cutting is implemented using an end mill. The surfaces of a medical device need to be so made that they inhibit adhesion of germs to the medical device and, when in contact with fluent blood, inhibit adhesion of platelets to the medical device and, hence, formation of blood clots. Cutting a titanium or titanium alloy base material surface with, for example, an end mill size-reduces crystal grains in the surface and leaves traces of cutting, thereby posing great problems in obtaining a surface inhibiting adhesion of germs as required of medical devices.

To address the above problems, the machining is followed by, for example, buffing, chemical etching, or blast polishing.

However, these processes in turn present their own problems: buffing is not applicable to a base material having a relatively complicated configuration; chemical etching exposes crystal grains of a base material; in blast polishing, pieces of a blasting material drive into a base material and remain in the base material surface. Polishing requires extended labor.

Until now, there is no known method of manufacturing a medical device using an electron beam irradiation process to reduce platelet adhesion of surfaces.

Japanese Patent Laid-open No. JP 2003-111778 and "Development of Dental Metal Surface Polishing Method using Electron Beam," a PhD dissertation by Junko TOKUNAGA, Graduate School of Dentistry, Osaka University, March 2008, disclose a known method involving subjecting a metallic base material of pure titanium, a metal used in dentistry, to electron beam irradiation for improved surface flatness, enhanced glossiness, and increased corrosion resistance.

However, when a material other than pure titanium, chiefly a 6-4 titanium material or the like, is subjected to electron beam irradiation for improved surface flatness, enhanced glossiness, and increased corrosion resistance in the same manner as used for pure titanium, impurities contained in the titanium material may develop small pits (hereinafter referred to as craters) in the outermost surface of the material as the outermost surface is caused to boil and vaporize by the electron beam irradiation, resulting in defects in the surface.

SUMMARY

According to one aspect, a method of manufacturing a medical device comprises subjecting a surface of a titanium base material or titanium alloy base material which has previously undergone at least a cutting process to electron beam irradiation to reduce platelet adhesion of the surface when the surface comes into contact with blood.

The method produces a medical device having a surface inhibiting adhesion of germs and which is exhibits reduced platelet adhesion when contacted by blood.

The method of manufacturing the medical device can involve performing the electron beam irradiation after the surface is heat-treated. The implementation of the electron beam irradiation can involve first performing electron beam irradiation using a first voltage and then performing a second electron beam irradiation using a second voltage that is higher than the first voltage.

The electron beam irradiation can be implemented first by reverse-polarity electron beam irradiation using a pure titanium metal as an anode, followed by straight-polarity electron beam irradiation.

A medical device obtained by another manufacturing method has a surface, which comes into contact with blood, with reduced platelet adhesion and which surface inhibits formation of small pits (so-called craters) in the surface caused by electron beam irradiation.

Another aspect of the disclosure here involves a method of manufacturing a medical device possessing a medical device configuration and configured to contact blood, wherein the method comprises: cutting the medical device from a base material so that the medical device possesses a medical device configuration, with the base material being either titanium or titanium alloy, and the cutting of the base material reducing a size of crystal grains of the titanium or titanium alloy; subjecting the medical device produced by cutting the base material to heat-treatment to thermally expand the crystal grains of the titanium or titanium alloy that were reduced in size by the cutting; and subjecting the outer surface of the medical device which was subjected to the heat-treatment to electron beam irradiation to reduce platelet adhesion to the outer surface of the medical device when the outer surface of the medical device contacts the blood.

In accordance with another aspect, a method of manufacturing a medical device possessing a medical device configuration and configured to contact blood comprises; cutting the medical device possessing the configuration from a titanium base material or titanium alloy base material to produce a medical device made of the titanium or the titanium alloy base material and possessing the medical device configuration; and electron beam irradiating the outer surface of the medical device possessing the medical device configuration to decrease surface roughness and thus reduce platelet adhesion to the outer surface of the medical device when the outer surface of the medical device contacts the blood.

BRIEF DESCRIPTION OF DRAWING FIGURES

FIGS. 1A-1C illustrate a metallic surface obtained as a comparative material in Example 1, wherein FIG. 1A is a metallographic micrograph showing the surface of the comparative material obtained in Example 1 (20× magnification), FIG. 1B is a laser micrograph showing the surface of the comparative material obtained in Example 1, and FIG. 1C is a diagram showing a measurement result of the surface roughness of the surface of the comparative material obtained in Example 1.

FIG. 14A is a surface micrograph acquired by a metallograph (20× magnification) and showing a surface obtained in a first stage in Example 4, and FIG. 14B is a surface micrograph acquired by a metallograph (20× magnification) and showing a surface obtained in a second stage in Example 4.

FIG. 15 is a schema of an electron beam irradiator with a reverse polarity.

FIG. 16 is a surface micrograph acquired by a metallograph (20× magnification) representing the surface of a base material subjected to 2-stage electron beam irradiation in Example 5.

FIGS. 17A and 17B illustrate a result of an abrasion-resistance test applied to a surface obtained in Example 3 and coated with DLC, wherein FIG. 17A illustrates Rockwell indentations and FIG. 17B illustrates abrasion marks.

FIGS. 18A and 18B illustrate a result of an abrasion-resistance test applied to a surface obtained in Example 4 and coated with DLC, wherein FIG. 18A illustrates a Rockwell indentation, and FIG. 18B illustrates abrasion marks.

FIGS. 19A and 19B illustrate a result of an abrasion-resistance test applied to a surface obtained in Example 5 and coated with DLC, wherein FIG. 19A illustrates a Rockwell indentation and FIG. 19B illustrates abrasion marks.

DETAILED DESCRIPTION

The method of manufacturing a medical device is described in detail below as one example of the inventive manufacturing method.

1. Titanium or Titanium Alloy Base Material

Titanium or titanium alloy base materials used for medical devices include pure titanium classified as JIS Class 1 and JIS Class 2 and Ti-6Al-4V (referred to below as 6-4 alloys), 6-4 alloy-based ELI materials (JIS Class 61), Ti-6Al-2Nb-1Ta, Ti-15Zr-4Nb-4Ta, Ti-6Al-7Nb, Ti-3Al-2.5V, Ti-13Nb-13Zr, Ti-15Mo-5Zr-3Al, Ti-12Mo-6Zr-2Fe, and Ti-15Mo.

2. Machining

A titanium or titanium alloy base material is made into, or configured as, a block material through, for example, a rolling process and then machined into a shape as used in a medical device. Machining may be implemented by a method as required for an individual medical device and is not particularly specified or limited. In the manufacturing method of the invention, machining is implemented at least by cutting using mostly an end mill.

Figure 1A:
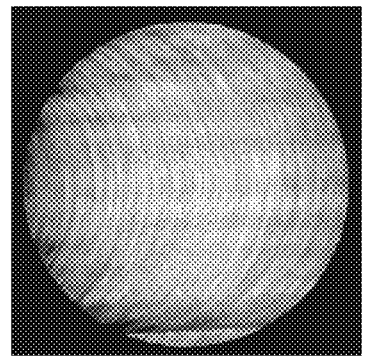
Figure 1B:
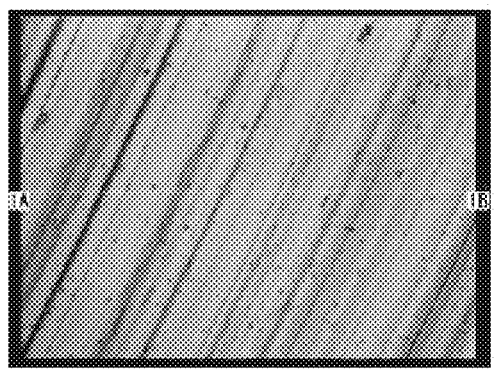
Figure 1C:
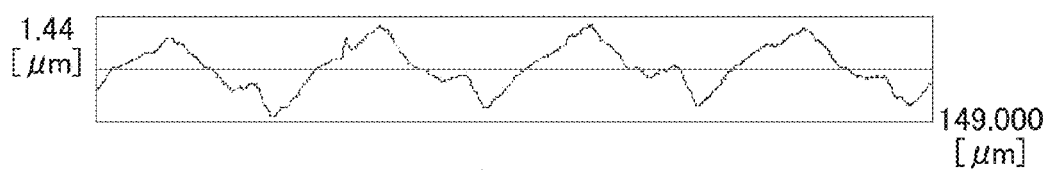
Figure 2A:
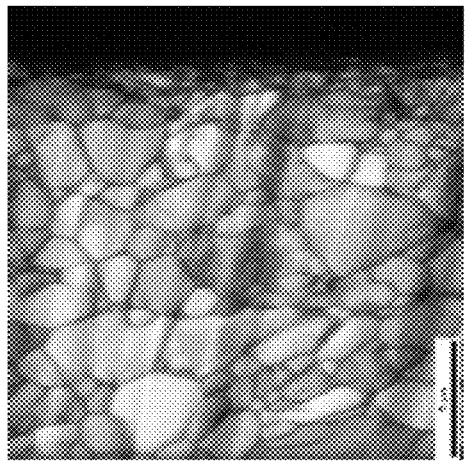
FIG. 2A is a photograph showing an image acquired by a TEM (transmission electron microscope) and representing a cross section of the comparative material obtained in Example 1.

FIG. 1A, FIG. 1B and FIG. 1C show results of an end-milled surface serving as a comparative material in Example 1 described later. When the titanium or titanium alloy base material is not pure titanium, traces of cutting are observed as illustrated in FIGS. 1A-1C. FIG. 2A shows an image acquired by a transmission electron microscope (TEM) and representing a cross section of an end-milled base material. Size reduction of crystal grains is also observed.

3. Electron Beam Irradiation

Figure 3:
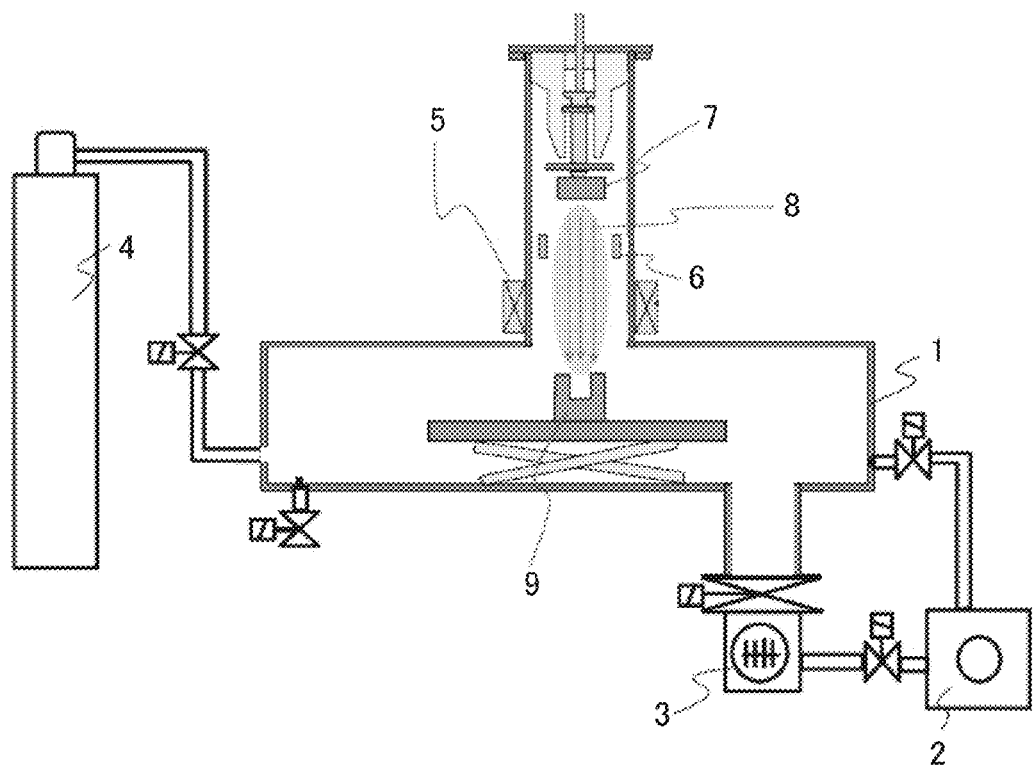
FIG. 3 is a schematic diagram explaining a large-area electron beam irradiator.

FIG. 3 illustrates a schematic assembly of an electron beam irradiator used in the method. FIG. 3 illustrates an electron beam irradiator using an explosive electron emission (EEE) method.

A sample 9 is placed in a vacuum chamber 1 in which the pressure has been reduced to a vacuum by a vacuum pump 2 and an auxiliary vacuum pump 3, and electrons emitted from a cathode 7 hit anode plasma 8 generated by an anode 6 to further generate electrons (Penning effect). The irradiator also includes a solenoid 5 and an argon gas container 4.

Electron beam irradiation is implemented preferably under the following conditions: applied cathode voltage $V_c = 10$ kV to 30 kV; solenoid voltage $V_s = 0.1$ kV to 1 kV; degree of vacuum in an electron gun, $P_i = 0.1$ Pa or less, preferably 0.01 Pa to 0.1 Pa; number of times an electron beam is applied (at about 0.2 Hz) $N = 1$ to 20; and distance from the lower tip of the electron gun to the base material $L = 5$ mm to 50 mm. The base material may have magnets attached to its bottom. When magnets are provided, an electron beam can be caused to focus.

Figure 4A:
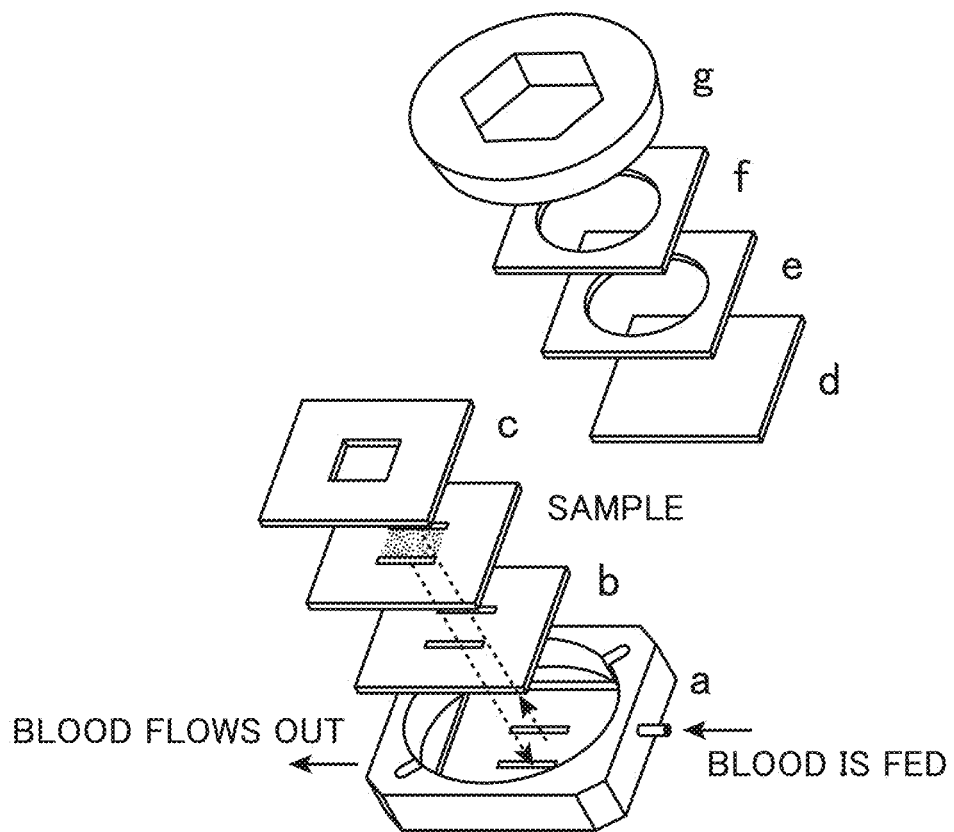
FIG. 4A is an exploded perspective view of a flow chamber.

4. Decrease in Platelet Adhesion of Surface in Contact with Blood Following Electron Beam Irradiation A titanium or titanium alloy base material subjected to electron beam irradiation in Step 3 above was held in a flow chamber, where blood modified to have a hematocrit of 40% and a platelet count of $1.5\times10^5/\mu L$ was refluxed to circulate at a flow rate of 6 ml/h for 10 minutes. The specimen of the titanium or titanium alloy base material recovered from the flow chamber was washed, and the platelets adhered to the surface were fixed, dehydrated, and lyophilized, whereupon the state of the platelets adhered to the surface and the shape change of platelets occurring with activation were observed with a scanning electron microscope (SEM). FIG. 4A illustrates, in an exploded perspective view, a structure of the flow chamber used.

Figure 4B:
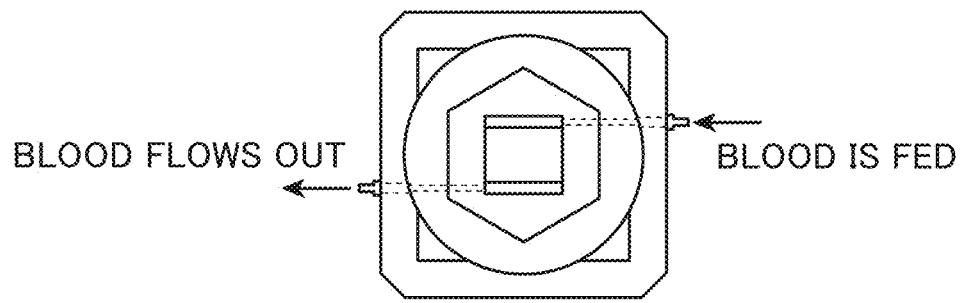
FIG. 4B is a top plan view of the flow chamber.

The flow chamber illustrated in FIGS. 4A and 4B comprises a silicone plate b, the titanium or titanium alloy base material, a Teflon™ spacer c, a coating slide glass plate d, a silicone plate e, and a metallic plate f, all fitted in this order into an acrylic substrate a and fastened together with a screw g tightened to a given torque. The Teflon™ spacer c has a cut-out square central portion (measuring e.g., 10 mm×10 mm). Blood supplied by a blood feeder such as a syringe pump through an inlet of the acrylic substrate passes through a gap between the coating slide glass plate and the titanium or titanium alloy base material, i.e., the cut-out portion of the Teflon™ spacer, and is discharged through an outlet of the acrylic substrate.

Figure 5A:
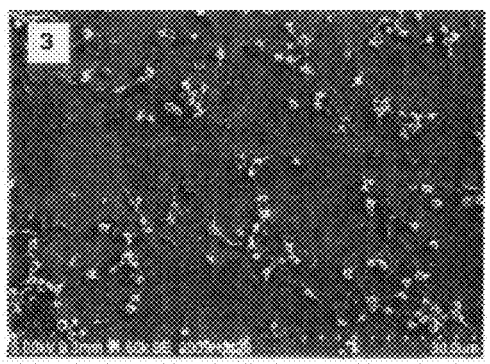
FIG. 5A is a micrograph showing platelets adherent to a specimen 1A.
Figure 6A:
FIG. 6A is a micrograph showing platelets adherent to a specimen 21A.

FIG. 5A illustrates platelets adhered to the specimen 1A not subjected to electron beam irradiation. FIG. 6A illustrates platelets adhered to the specimen 21A subjected to electron beam irradiation. It is apparent from a comparison of the two that the titanium or titanium alloy base material surface has a platelet adhesion that is considerably reduced by the electron beam irradiation. After the electron beam irradiation, not only does the surface have a reduced count of adhered platelets, but activation of platelets is inhibited on the surface as illustrated in Examples described later.

Observation of Craters

Figure 8:
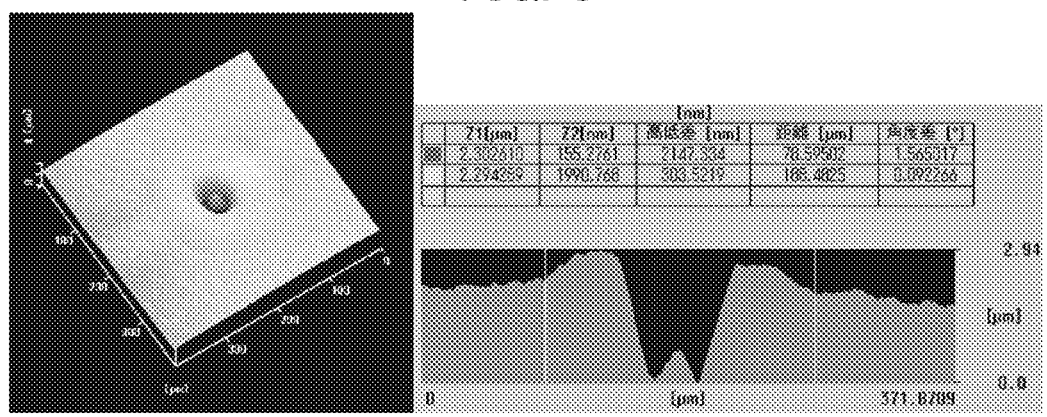
FIG. 8 shows a crater as observed with an atomic force microscope.
Figure 9:
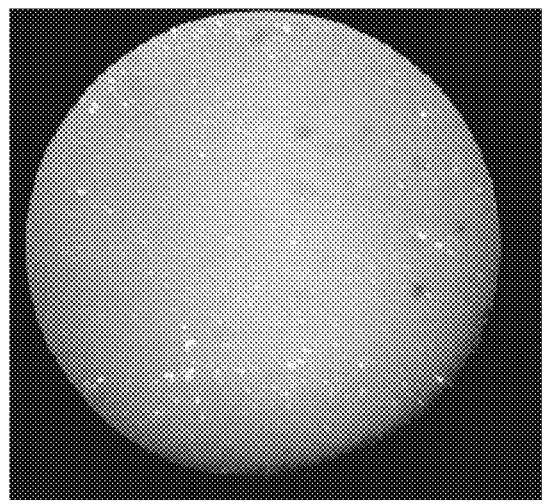
FIG. 9 is a photograph showing craters in a surface as observed with a metallograph (20× magnification).

It was shown that the method in which end milling of the titanium or titanium alloy base material is followed by the electron beam irradiation proved to yield a titanium or titanium alloy base material surface that, when in contact with blood, has a reduced platelet adhesion. However, observation of the titanium or titanium alloy base material surface revealed defects called craters that were caused depending on conditions. FIG. 8 shows a crater observed with atomic force microscopy (referred to as "AFM" below). FIG. 9 is a metallographic micrograph (20× magnification) showing a surface having craters.

The craters have a depth of about 2.1 μm and is considered to have been caused by impurities inside the base material or matter that might have fallen from above the base material due to electron beam irradiation. It was also found by observation that the frequency at which craters are generated during the electron beam irradiation following the machining changes depending on machining speed, machining means, and applied load.

When the titanium or titanium alloy base material surface has small pits (so-called craters) that may be caused by electron beam irradiation, the surface, when in contact with blood as the base material is used in a medical device, is liable to retain blood or allow a blood clot to form, impairing its biocompatibility.

5. Reduction of Craters

It was found that when the surface is subjected to heat treatment in a process preceding the electron beam irradiation, the craters generated during the electron beam irradiation can be reduced. This is considered to be attributable to thermal expansion of crystal grains that were reduced in size by the cutting process.

Any one of the following methods may be implemented:
(1) a method involving vacuum-annealing the titanium or titanium alloy base material surface after the cutting process, wherein vacuum annealing is implemented under conditions for example, that the degree of vacuum $P=8\times10^{-3}$ Pa, preferably 0.001 Pa to 0.1 Pa, and the holding temperature× time=800° C.×1 hour, preferably 500° C. to 900° C. for 30 minutes to 3 hours, followed by slow cooling to a room temperature, the vacuum annealing being followed by the electron beam irradiation, and
(2) a plasma cathode electron beam irradiation method.

Figure 10:
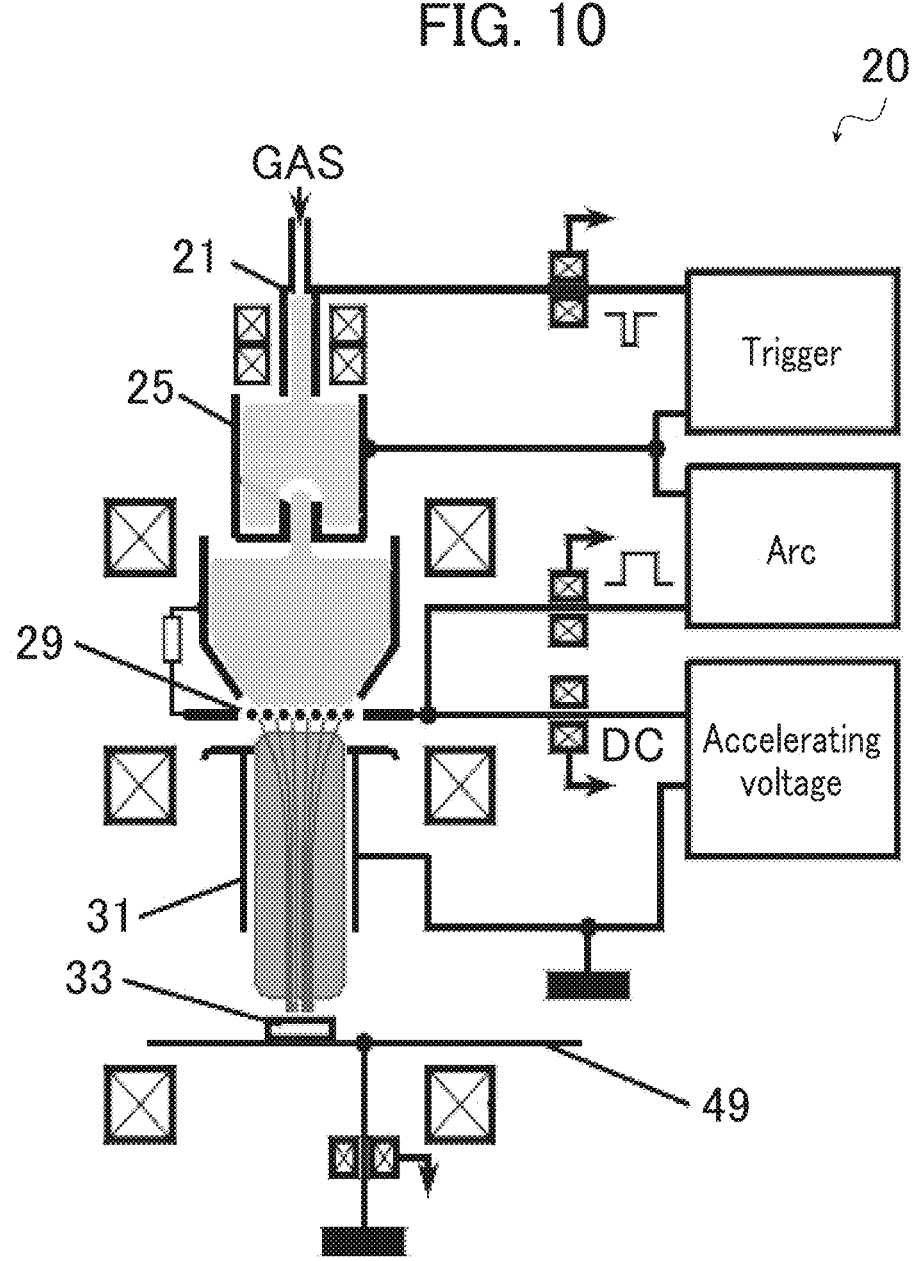
FIG. 10 is a schematic diagram for explaining a SOLO system.

As a plasma cathode electron beam irradiator, use may be made of, for example, SOLO (electron beam generator manufactured by Nagata Seiki Co, Ltd.). FIG. 10 is a schematic of such device. As shown in FIG. 10, SOLO comprises a hollow cathode 21 and a hollow anode 25 to generate plasma, which serves as a cathode. An electron beam passes through a DC-biased grid 29 for acceleration, passes through a drift tube 31, and irradiates a sample 33 on a holder 49. An electron beam having an irradiation area measuring 1 mm to 10 mm in diameter near the sample, which is a titanium or titanium alloy base material, scans the sample.

Figure 2B:
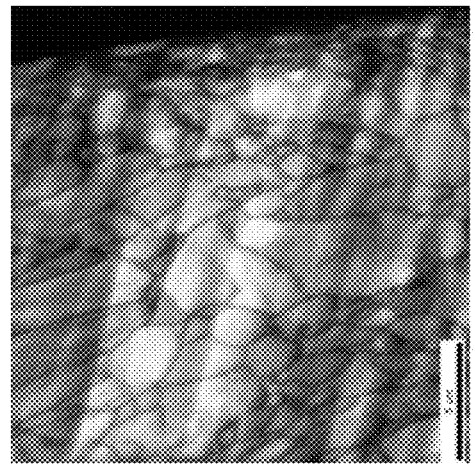
FIG. 2B is a photograph showing an image acquired by a TEM and representing a cross section of a base material irradiated by SOLO system.

An end-milled surface of a 6-4 alloy is scanned with a plasma cathode electron beam preferably using the SOLO system 20 illustrated in FIG. 10 under the following conditions:

Cathode current I=50 A to 200 A; acceleration voltage Vacc=10 kV to 30 kV; degree of vacuum, or Ar gas pressure, in an electron gun, $P_t=1\times10^{-2}$ Pa to $10\times10^{-2}$ Pa; number of times an electron beam is applied at about 0.5 Hz to 20 Hz, $N_t=1000$ to 5000; and frequency f=0.5 Hz to 20 Hz. A cover made of titanium foil is provided above the base material. After irradiation, the sample is slowly cooled inside the irradiator. FIG. 2B illustrates an image acquired by a TEM showing a cross section of a base material irradiated by SOLO in Example 2. FIG. 2A shows size reduction of crystal grains that occurred after the cutting process; FIG. 2B shows enlargement of crystal grains that occurred after the irradiation by SOLO. The inventors infer that the enlargement of crystal grains reduced the crystal grain boundary and caused impurities to float from the base material, so that the occurrence of craters is inhibited during the electron beam irradiation to follow.

6. Electron Beam Irradiation after Crater Reduction Process

The same electron beam irradiation as in Step 3 above is applied. Step 5 above and Step 6 yield a titanium or titanium alloy base material surface having a reduced platelet adhesion when in contact with blood and an inhibited occurrence of craters.

7. Multistage Electron Beam Irradiation

After end milling, first electron beam irradiation is implemented with a relatively low cathode voltage, followed by second electron beam irradiation with a cathode voltage that is higher than that used in the first electron beam irradiation.

The first electron beam irradiation is preferably implemented with a first cathode voltage applied, Vc=5 kV to 20 kV. Other conditions are not specifically limited in the first electron beam irradiation. For example, it is preferable that solenoid voltage Vs=0.1 kV to 1 kV; degree of vacuum in an electron gun, $P_t=0.1$ Pa or less (no lower limit is specifically specified but because a high degree of vacuum is uneconomical, a range of 0.01 Pa to 0.1 Pa may be used); number of times an electron beam (at about 0.2 Hz) is applied, N,=1 to 20; and distance from the lower tip of the electron gun to the base material, L,=5 mm to 50 mm.

The second electron beam irradiation is implemented with a cathode voltage that is 5 kV to 10 kV higher than that of the first electron beam irradiation.

While conditions other than the cathode voltage are not particularly specified, the same conditions may be used as in the first electron beam irradiation.

8. Pure Titanium is Used as an Anode to Implement Electron Beam Irradiation in Reverse Polarity.

Pure titanium is used as an anode to implement electron beam irradiation in reverse polarity. FIG. 15 is a schematic of an irradiator used. The irradiator is basically the same as the electron beam irradiator illustrated in FIG. 3.

In FIG. 15, a base material (sample) is disposed at an upper cathode 70, and pure titanium is disposed at a lower anode 72. The upper cathode is the base material; the lower target is pure titanium. While irradiation conditions are not particularly specified, it is preferable that the cathode voltage is relatively high with Vc=20 kV to 30 kV, and the number of irradiations N=10 to 60 at 0.1 Hz to 1 Hz.

In the process, the inventors observed not only that the titanium from the lower anode was deposited by sputtering on the cathode base material surface but that impurities were ejected explosively from near the surface of the upper cathode base material, creating cathode spots.

Thereafter, the multistage electron beam irradiation described in Step 7 above is preferably applied. The one-stage electron beam irradiation described in Step 2 above may instead be applied.

9. Surface Coating Method

The titanium or titanium alloy base material surface obtained in any of Steps 3 to 8 above may be further coated with a thin film composed of a substance different from the titanium or titanium alloy base material. Examples of the substance for coating the surface include organic substances such as diamond-like carbon (DLC) deposited by chemical vapor deposition (CVD), DLC deposited by physical vapor deposition (PVD), and PTFE.

Coating a surface-treated titanium or titanium alloy base material with a thin film composed of a substance different from the titanium or titanium alloy base material produces additional effects of lowering the static friction coefficient of the surface, preventing scratches from occurring, and enhancing antithrombogenicity. Evaluation was made to determine whether, when the base material surface is coated with a thin film composed of a substance different from the base material, the above electron beam irradiation poses any problem to the thin film deposition process. As described in detail below in Example 6 with reference to an example of a diamond-like carbon (DLC) coat deposited by PVD, adhesion between the film deposited as an upper layer and the electron beam-irradiated titanium or titanium alloy base material was examined. The results obtained in Example 6 show that the electron beam irradiation of the invention does not pose any problem to the deposition of the thin film as an upper layer.

10. Medical Device

The kind and the structure of the medical device obtained by the manufacturing method disclosed here are not specifically limited. The medical device comprises a machined metallic surface that comes into contact with blood, body fluid, or tissue. Examples of the medical device with which the disclosure here, including the manufacturing method, is usable include a pump in an artificial heart lung system; a blood pump; a cardiac pacemaker; a denture, an artificial bone, a bolt for implant, and other implants; a guide wire; and a stent. More specifically, examples include a stent and a blood pump made using a titanium material or a titanium alloy.

Figure 20:
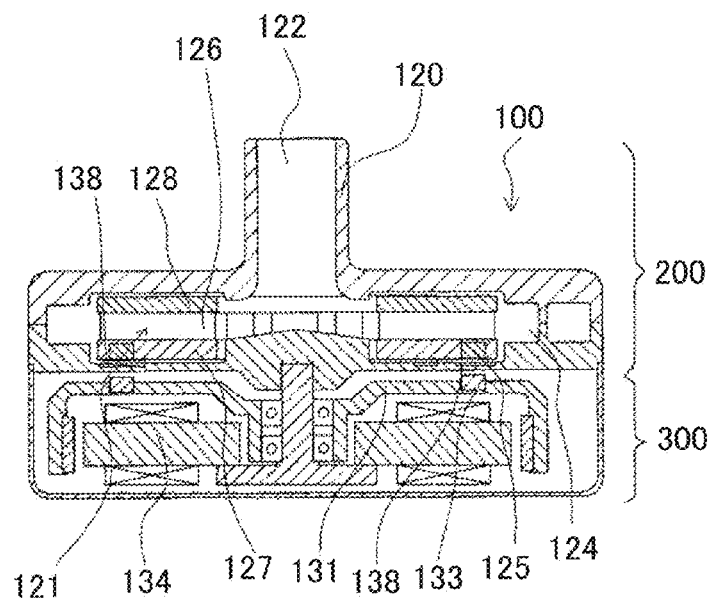
FIG. 20 is a longitudinal cross-sectional view of a centrifugal blood pump device described in Japanese Application Publication No. 2005-270345.
Figure 21:
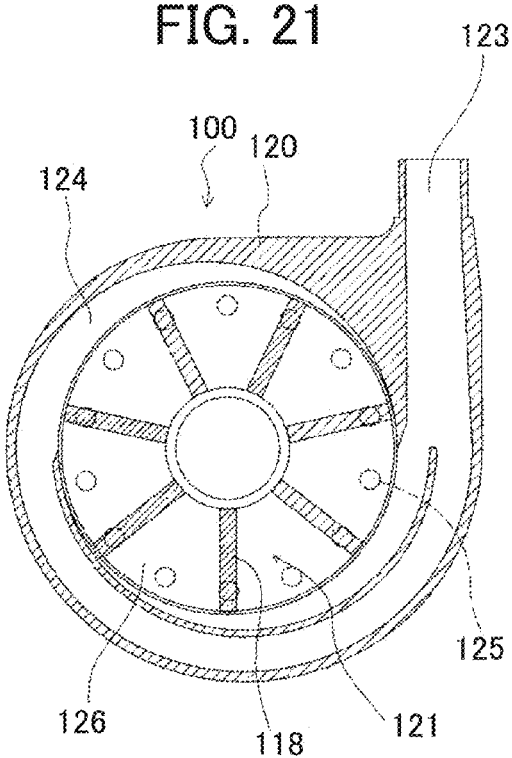
FIG. 21 is a transverse cross-section of the centrifugal blood pump device described in JP 2005-270345.
Figure 22:
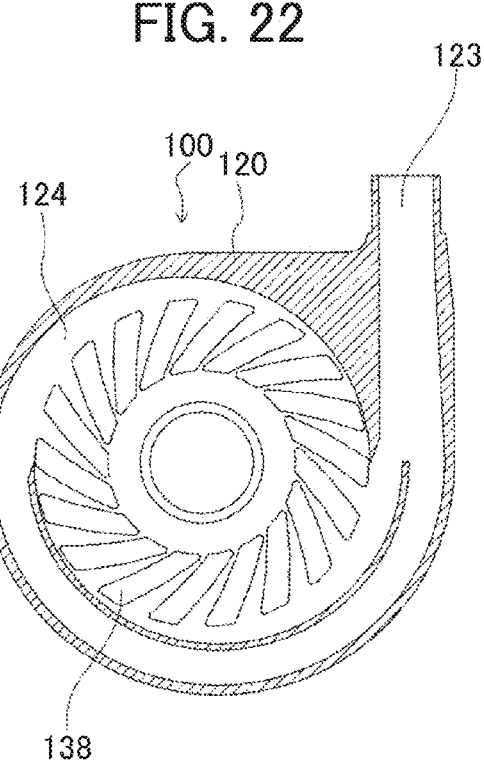
FIG. 22 is a cross section showing the centrifugal blood pump device of FIG. 21 with the impeller removed.

A more specific example of the medical device with which the disclosure here, including the manufacturing method, is usable is shown in FIGS. 20-22. Here, a blood pump device 100 comprises: a housing 120 including a blood inlet port 122 and a blood outlet port 123; a pump section 200 including an impeller 121 provided with magnetic members 125 and adapted to turn inside the housing 120 to feed blood; and an impeller turning torque generator 300 adapted to suck and turn the impeller 121 of the pump section 200, wherein the pump section 200 further includes dynamic pressure grooves 138 provided in the housing's inner surface on the impeller turning torque generator 300 side or in the surface of the impeller which is on the impeller turning torque generator 300 side, and wherein the impeller 121 turns out of contact with the housing 120. A blood pump device having such features is described in more detail in Japanese Application Publication No. 2005-270345 and Japanese Application Publication No. 2005-287598.

The blood pump with which the disclosure here, including the manufacturing method, is usable is not specifically limited. Describing the centrifugal blood pump device 100 illustrated in FIGS. 20-22 as one example, magnetic members are embedded in the impeller 121 of the blood pump, and the impeller 121 is turned by the rotation of a rotor 131 of an impeller turning torque generator 300. The rotor 131 is rotated by a motor 134. The rotor 131 has magnets 133 and is turned or rotated without contacting the inner surface of the housing 120 owing to a pressure generated by dynamic pressure grooves 138 during rotation as illustrated in FIGS. 20-22.

The housing 120 is made of non-magnetic substance such as a titanium or titanium alloy base material and comprises a blood chamber 124. The housing 120 accommodates the impeller 121. As illustrated in FIG. 21, the blood outlet port 123 projects in a tangential direction from a lateral portion of the housing 120 which possesses a substantially cylindrical shape.

As illustrated in FIG. 20, the blood chamber 124 in the housing 120 accommodates the impeller 121 which is disk-shaped with a centrally located through-hole. The impeller 121 comprises an annular plate member 127 (lower shroud) forming a lower surface, an annular plate member 128 (upper shroud) forming an upper surface and having a centrally located opening, and a plurality of vanes 118 provided between the plate members 127, 128. Between the lower shroud and the upper shroud, there are formed a plurality of blood passages 126 divided by adjacent vanes 118. The blood passages 126 communicate with the central opening of the impeller 121 and extend from the central opening of the impeller 121 to the outer periphery, each with a gradually increasing width, as illustrated in FIG. 21.

The impeller turning torque generator 300 of the blood pump 100 in this example is totally free from contact with blood. By contrast, the inner surfaces of the housing section on the blood inlet port side and the housing section on the torque generator side, the dynamic pressure grooves provided in one or both of the housing sections, and, where necessary, the impeller, as well as other components where necessary, are provided with, for example, a cover made of a titanium or titanium alloy base material, these components having surfaces that come into contact with blood. Where these components have a titanium or titanium alloy base material surface subjected to at least a cutting process, and when manufactured by the method disclosed here, the platelet adhesion of the surfaces that come into contact with blood can be reduced, and so the utility of the medical device is enhanced.

Further, the manufacturing method disclosed here helps enable production of a highly biocompatible blood pump device that reduces the platelet adhesion of a surface coming into contact with blood and inhibits the formation of craters, reducing the defects of permitting collection of blood or easy formation of blood clots on the surface in contact with blood.

EXAMPLES

The manufacturing method disclosed here is described in different detail below with reference to Examples. It is to be understood that the scope of the invention here is not limited by the Examples.

Example 1

1. End Milling

The surface roughness of an end-milled surface of an ELI base material (manufactured by Allegheny Ludlum NJ USA, Grade 23) (specimen No. 1A) was observed with a metallograph and a laser microscope; the photographs obtained are shown respectively in FIG. 1A (20× magnification) and FIG. 1B. In both photographs, traces of machining were clearly observed.

The end milling was implemented using MTV515/40N, a high-speed machining center manufactured by YAMAZAKI MAZAK CORPORATION at a turning speed of 750 rpm and a feed rate of 30 mm/min. for 30 minutes.

The surface roughness, shown in FIG. 1C, was measured using Nanopics 1000 manufactured by Seiko Instruments Inc. A span of 149 μm was also among the measuring conditions.

FIG. 2A shows a photograph of an image acquired by a TEM (transmission electron microscope) representing a cross section of an end-milled base material. It was observed that crystal grains before the machining decreased in size through the cutting process.

2. Electron Beam Irradiation

Apart from the above, a 6-4 alloy was end-milled under the same conditions as in Step 1 above to obtain the specimen No. 21A, which underwent electron beam irradiation by a large-area electron beam irradiator illustrated in FIG. 3 under the following conditions: applied cathode voltage Vc=17 kV, solenoid voltage Vs=0.5 kV, degree of vacuum in an electron gun P=0.05 Pa, number of times an electron beam is applied (at about 0.2 Hz), $N_i$=7, and distance from the lower tip of the electron gun to the base material, $L_i$=20 mm. The surface roughnesses of the specimen No. 1A, an ELI material that was end-milled but not subjected to electron beam irradiation, and the 6-4 alloy, which was end-milled and subjected to electron beam irradiation using the large-area electron beam irradiator illustrated in FIG. 3, were measured. The obtained surface roughnesses were compared as shown in Table 1.

An ELI material was used as the specimen No. 1A (hereinafter referred to as specimen 1A) and a 6-4 alloy was used as the specimen No. 21A (hereinafter referred to as specimen 21A) in order to show that, in examples where electron beam irradiation of the invention is implemented, similar results are obtained regardless of whether one may use a 6-4 alloy having a lower purity or an ELI material, the specimen 1A being used as a comparative material for showing that traces of end-milling are left.

The obtained measurements of surface roughness are as follows. The same measuring conditions were used as in the measuring implemented after machining described in Step 1 above.

TABLE 1

| Specimen No. | Measuring distance (μm) | Ra(μm) | Ry(μm) | Rz(μm) |
|---|---|---|---|---|
| 1A | 149 | 0.539 | 2.640 | 2.008 |
| 21A | 149 | 0.083 | 0.370 | 0.266 |

3. Platelet Adhesion Test

Observation of Adhered Platelets

The obtained specimens 1A and 21A were each held beneath the Teflon™ spacer in the flow chamber illustrated in FIG. 4, and blood modified to have a hematocrit value of 40% and a platelet count of $1.5 \times 10^5$/μl was refluxed to circulate at a flow rate of 6.0 ml/h for 10 minutes. The specimens were recovered from the flow chambers, whereupon washing, fixing the platelet, dehydration, and lyophilization were carried out. FIGS. 5 and 6 show photographs representing the adhered platelets of the specimen surfaces as observed with a scanning electron microscope (SEM).

Figure 5B:
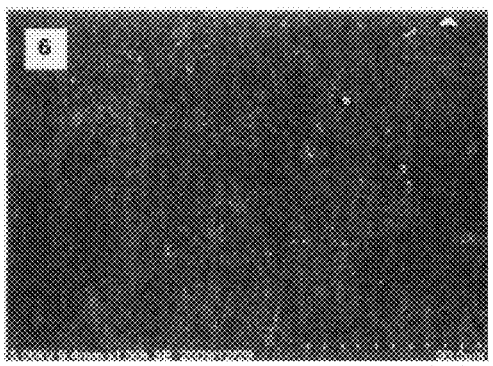
FIG. 5B is a photograph acquired under the same conditions for comparison to show a metallic surface that is out of contact with blood flow.

FIG. 5A shows the platelets adhered to the specimen 1A. FIG. 5B shows a metallic surface of another specimen 1A that is not in contact with blood flow for comparison.

Figure 6B:
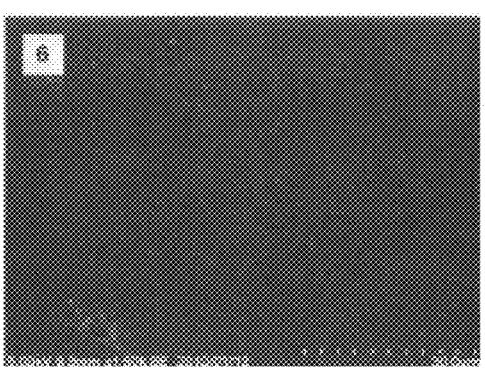
FIG. 6B is a photograph acquired under the same conditions for comparison to show a metallic surface that is out of contact with blood flow.

FIG. 6A shows the platelets adhered to the specimen 21A. FIG. 6B shows a metallic surface of another specimen 21A that is not in contact with blood flow for comparison.

It is apparent that the specimen 21A subjected to the electron beam irradiation shows a smaller number of platelets adhered to the surface in comparison with the end-milled specimen 1A which has not been subjected to electron beam irradiation.

Evaluation of Platelet Shape Change Associated with Activation

Figure 7:
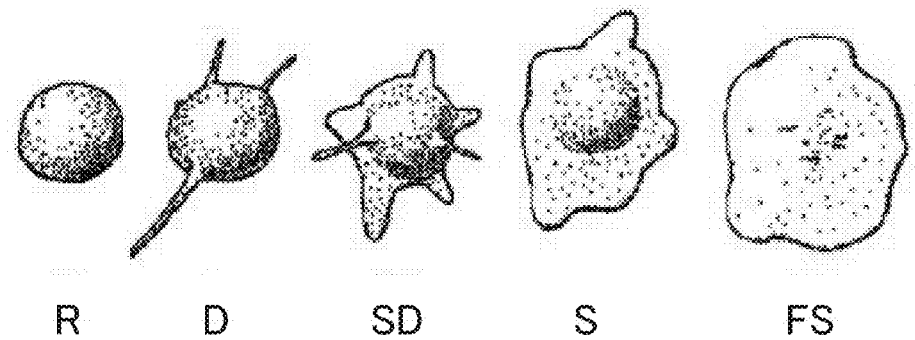
FIG. 7 is a schematic diagram illustrating shape change of a platelet as it is activated.

Platelet shape change associated with platelet activation was observed from the results obtained in FIGS. 5 and 6. FIG. 7 schematically illustrates shape change of a platelet associated with its activation, where the shape change is broken down into five forms defined as follows: R: Round; D: Dendritic; SD: Spread Dendritic; S: Spreading; and FS: Fully Spread. The definition is made according to the classification described by Steven L. Goodman in FIG. 11 of J. Biomed Mater Res, 45, 240-250 (1999). Note that "A" is used in the above literature in lieu of "R".

TABLE 2

| Test piece No. | R | D | SD | S | FS | Total |
|---|---|---|---|---|---|---|
| 1A | 0 | 22 | 23 | 23 | 15 | 83 |
| 21A | 1 | 13 | 8 | 6 | 6 | 34 |

Table 2 shows the numbers of the respective forms of platelets resulting from shape change occurring in association with activation in a field of view of $1.25 \times 10^4$ μm2.

It is apparent from the results shown by Table 2 that the titanium or titanium alloy base material surfaces subjected to the electron beam irradiation after the machining not only had smaller numbers of adhered platelets, but platelet shape change occurred less, indicating that the activation of platelets was inhibited.

Example 2

The surface of a 6-4 alloy that was end-milled as in Example 1 was scanned with a plasma cathode electron beam using the SOLO system 20 illustrated in FIG. 10 under the following conditions:

Cathode current I=100 A; acceleration voltage Vacc=15 kV; degree of vacuum and Ar gas pressure in an electron gun, P,=3.5×10$^{-2}$ Pa; number of times an electron beam (having an irradiation area measuring about 5 mm in diameter near the base material) is applied at a frequency of about 20 Hz, N,=5,000. A cover made of titanium foil was provided above the base material. After irradiation by SOLO, the sample was slowly cooled inside the irradiator.

FIG. 2B illustrates an image acquired by a TEM and shows a cross section of a SOLO-irradiated base material. On the 6-4 alloy surface end-milled in Example 1 (comparative material), crystal grains decreased in size after the cutting process as observed in FIG. 2A whereas enlargement of crystal grains occurred after SOLO irradiation as observed in FIG. 2B. The plasma cathode electron beam irradiation was implemented, followed by electron beam irradiation using the irradiator illustrated in FIG. 3 under the following conditions:

Vc=20 kV, Vs=0.5 kV, P=0.05 Pa, N=15, and L=20 mm. In addition, magnets were provided at the bottom of the base material.

Figure 11A:
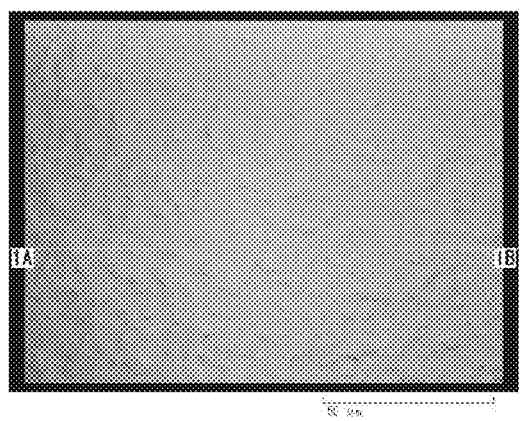
FIG. 11A is a photograph acquired by a laser microscope and showing a result obtained by irradiation with SOLO system and subsequent electron beam irradiation in Example 2.
Figure 12:
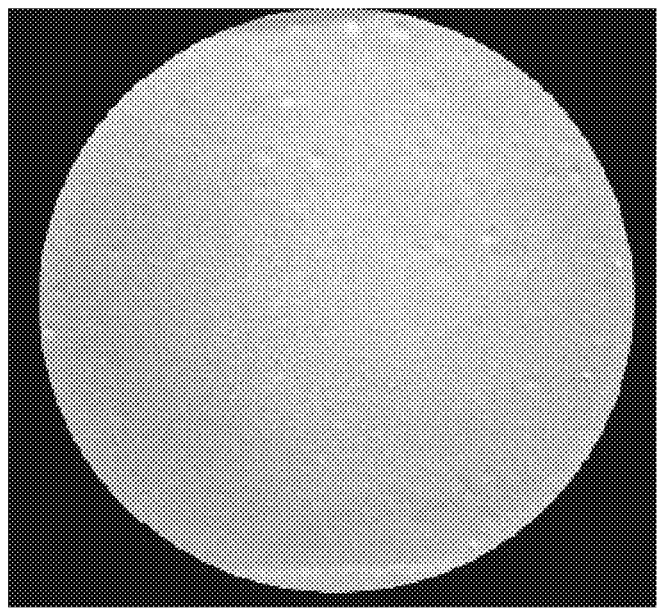
FIG. 12 is a metallographic micrograph (20× magnification) showing a surface obtained by irradiation with SOLO system and subsequent electron beam irradiation in Example 2.

FIG. 11A shows the resultant surface of the base material observed with a surface laser microscope. FIG. 12 shows an image of the base surface acquired in a broad range by a metallograph (20× magnification).

Figure 11B:
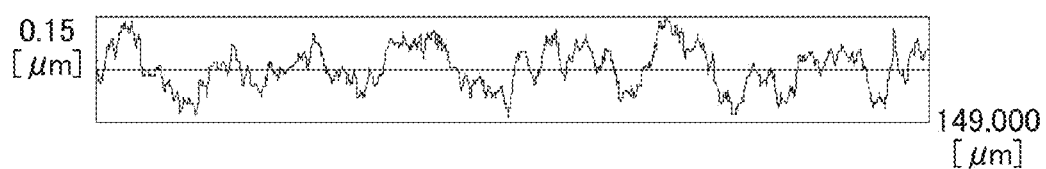
FIG. 11B is a diagram showing a measurement result of the surface roughness of the surface shown in FIG. 11A.

FIG. 11B shows measurements of surface roughness. Measurements of surface roughness obtained include:
Ra: 0.055 μm, Ry: 0.290 μm, and Rz: 0.262 μm, over a distance of 149.00 μm.

Example 3

Figure 13:
FIG. 13 is a surface micrograph representing the texture of a metal resulting from a process implemented in Example 3.

After end-milling, plasma cathode electron beam irradiation was implemented with SOLO as in Example 2 above except that an ELI material was used as titanium or titanium alloy base material, followed by the same electron beam irradiation as implemented in Example 2. FIG. 13 shows a photograph representing the result as acquired by a surface microscope.

Example 4

A 6-4 alloy was end-milled under the conditions used in Example 1 and thereafter subjected to the first electron beam irradiation with a relatively low voltage of 17 kV. Electron beam irradiation was effected under conditions as follows: applied cathode voltage Vc=17 kV, solenoid voltage Vs=0.5 kV, degree of vacuum in an electron gun, P,=0.05 Pa, number of times an electron beam is applied (at about 0.2 Hz), N,=10, and distance from the lower tip of the electron gun to the base material L=20 mm.

Subsequently, the second electron beam irradiation was implemented with 25 kV, a voltage that is higher than that used in the first electron beam irradiation. Electron beam irradiation was effected under conditions as follows: applied cathode voltage Vc=25 kV, solenoid voltage Vs=0.5 kV, degree of vacuum in an electron gun, P,=0.05 Pa, number of times an electron beam is applied (at about 0.2 Hz), N,=10, and distance from the lower tip of the electron gun to the base material L=20 mm.

FIG. 14A shows a surface micrograph (20× magnification) acquired by a metallograph and representing a base material surface after the first electron beam irradiation; FIG. 14B shows a surface micrograph (20× magnification) acquired by a metallograph and representing the base material surface after the second electron beam irradiation following the first electron beam irradiation. In FIG. 14A, a number of craters and traces of machining were detected. In FIG. 14B, traces of machining were not seen, and the number of craters decreased.

Example 5

The irradiator illustrated in FIG. 15 was used sample, the specimen 1A obtained by end-milling an ELI material in Example 1, was disposed at the upper cathode 70, and pure titanium was disposed at the lower anode 72. Electron beam irradiation was implemented with a cathode voltage of Vc=28 kV, N=40 times over. In the process of melt and cooling during the first electron beam irradiation, MnS or MC-based carbide for example, are produced immediately beneath craters. Reverse-polarity electron beam irradiation is considered to produce effects of blowing away the above products as an electron beam is applied.

In the process using reverse polarity, the inventors observed not only that the titanium arriving from the lower anode was deposited by sputtering on the cathode product but that impurities were ejected explosively from near the surface of the upper cathode product, creating cathode spots.

Subsequently, two-stage electron beam irradiation was implemented under the same conditions as in Example 4. FIG. 16 shows a surface micrograph (20× magnification) of the resultant base material surface acquired by a metallograph. The result shown in FIG. 16 revealed no craters. The entire irradiation implemented consisted of [reverse-polarity irradiation (28 kV)–straight polarity irradiation (17 kV)–straight polarity irradiation (25 kV)].

Example 6

The surfaces of the titanium or titanium alloy base materials obtained in Examples 3 to 5 were coated with diamond-like carbon (DLC).

The coating was implemented by GPAS (Graphite Pulse Arc Sputtering) method (U.S. Pat. No. 6,753,042). The DLC films on equivalent specimens had a thickness in a range of 1.0 μm to 1.2 μm.

A Rockwell indenter was press-inserted to examine the adhesion of the DLC film, the surface coating material, and a high-speed reciprocating motion was caused with a load applied to the indenter to evaluate the abrasion in order to examine the abrasion resistance. The Rockwell indenter was press-inserted with 150 kg, and the abrasion was evaluated by causing a reciprocating motion using a HEIDON Type 14DRa, a tribo-tester manufactured by Shinto Scientific Co., Ltd., with a load of 100 g, at a speed of 1,200 mm/min, and with a stroke of 6 mm, 2000 times over.

Figures 18A, 18B:
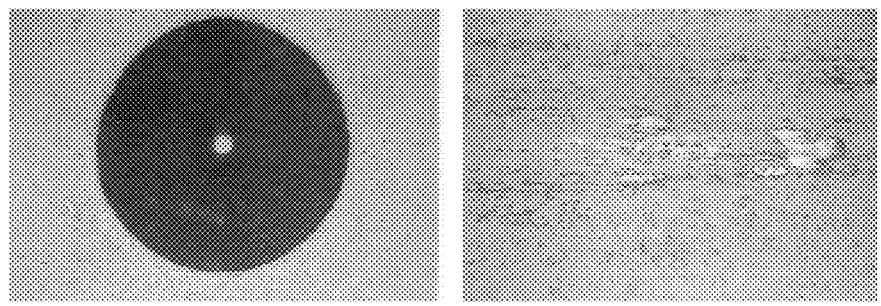
Figures 19A, 19B:
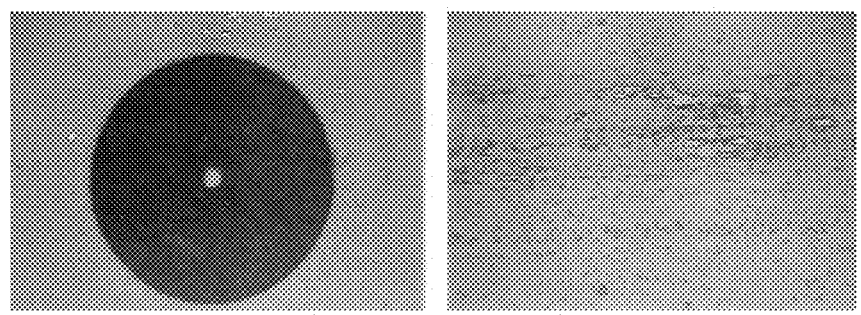

Results are shown in FIGS. 17 to 19. FIGS. 17A, 18A, and 19A show the resultant Rockwell indentations; FIGS. 17B, 18B, and 19B show the results of abrasion resistance evaluation.

In the case shown in FIG. 17 illustrating a surface obtained in Example 3 and coated with DLC, some detachments were observed near the Rockwell indentation but the adhesion posed no practical problems.

In the case shown in FIG. 18 illustrating a surface obtained in Example 4 and coated with DLC, adhesion was judged to pose no practical problems.

In the case shown in FIG. 19 illustrating a surface obtained in Example 5 and coated with DLC, adhesion was excellent.

Comparative Example 1

Pure titanium was deposited by magnetron sputtering on the surface of the specimen 1A obtained in Example 1. In this case, the sputtered film detached in the subsequent electron beam irradiation process, and the surface thus obtained was of no practical use.

The detailed description above describes various embodiments of the method for manufacturing a medical device. But it is to be understood that the invention is not limited to those precise embodiment and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A method of manufacturing a medical device possessing a medical device configuration and configured to contact blood, the method comprising:
   cutting the medical device from a base material so that the medical device possesses a medical device configuration, the base material being either titanium or titanium alloy, the medical device produced by the cutting possessing an outer surface, and the cutting of the base material reducing a size of crystal grains of the titanium or titanium alloy;
   subjecting the medical device produced by cutting the base material to heat-treatment to thermally expand the crystal grains of the titanium or titanium alloy that were reduced in size by the cutting; and
   subjecting the outer surface of the medical device which was subjected to the heat-treatment to electron beam irradiation to reduce platelet adhesion to the outer surface of the medical device when the outer surface of the medical device contacts the blood.

2. The method of manufacturing the medical device according to claim 1, wherein the subjecting of the outer surface of the medical device to electron beam irradiation comprises subjecting the outer surface of the medical device to a first electron beam irradiation using a first voltage and then subjecting the outer surface of the medical device to a second electron beam irradiation using a second voltage that is higher than the first voltage.

3. The method of manufacturing the medical device according to claim 1, further comprising coating the outer surface of the medical device with a film of material made of a composition different from the base material, the coating of the outer surface of the medical device with the film being performed after the electron beam irradiation.

4. The method of manufacturing the medical device according to claim 1, wherein the medical device is a part of a blood pump.

5. A method of manufacturing a medical device possessing a medical device configuration and configured to contact blood, the method comprising:
   cutting the medical device possessing the configuration from a titanium base material or titanium alloy base material to produce a medical device made of the titanium or the titanium alloy base material and possessing the medical device configuration, the medical device produced by the cutting possessing an outer surface; and
   electron beam irradiating the outer surface of the medical device possessing the medical device configuration to decrease surface roughness and thus reduce platelet adhesion to the outer surface of the medical device when the outer surface of the medical device contacts the blood.

6. The method of manufacturing the medical device according to claim 5, wherein the electron beam irradiation of the outer surface of the medical device possessing the medical device configuration comprises electron beam irradiating the outer surface of the medical device possessing the medical device configuration to a first electron beam irradiation using a first voltage and subsequently electron beam irradiating the outer surface of the medical device possessing the medical device configuration to a second electron beam irradiation using a second voltage that is higher than the first voltage.

7. The method of manufacturing the medical device according to claim 5, further depositing a coating on the outer surface of the medical device which has been electron beam, the coating being comprised of a material different from the titanium base material and titanium alloy base material, the coating being selected to, at least one of, lower static friction coefficient of the outer surface, prevent scratches from occurring on the outer surface and enhancing antithrombogenicity of the medical device.

8. A method of manufacturing a medical device comprising subjecting a surface of a titanium base material or titanium alloy base material which has previously undergone at least a cutting process to electron beam irradiation to reduce platelet adhesion of the surface when the surface comes into contact with blood.

9. The method of manufacturing the medical device according to claim 8, further comprising heat-treating the surface of the titanium base material or titanium alloy base material before the surface is subjected to the electron beam irradiation.

10. The method of manufacturing the medical device according to claim 9, wherein the subjecting of the surface of the titanium base material or titanium alloy base material to electron beam irradiation comprises subjecting the surface of the titanium base material or titanium alloy base material to a first electron beam irradiation using a first voltage and then subjecting the surface of the titanium base material or titanium alloy base material to a second electron beam irradiation using a second voltage that is higher than the first voltage.

11. The method of manufacturing the medical device according to claim 2, wherein the electron beam irradiation comprises reverse-polarity electron beam irradiation using a pure titanium metal as an anode, followed by straight-polarity electron beam irradiation.

12. The method of manufacturing the medical device according to claim 8, wherein the subjecting of the surface of the titanium base material or titanium alloy base material to electron beam irradiation comprises subjecting the surface of the titanium base material or titanium alloy base material to a first electron beam irradiation using a first voltage and then subjecting the surface of the titanium base material or titanium alloy base material to a second electron beam irradiation using a second voltage that is higher than the first voltage.

13. The method of manufacturing the medical device according to claim 12, wherein the electron beam irradiation comprises reverse-polarity electron beam irradiation using a pure titanium metal as an anode, followed by straight-polarity electron beam irradiation.

14. The method of manufacturing the medical device according to claim 8, wherein the electron beam irradiation comprises reverse-polarity electron beam irradiation using a pure titanium metal as an anode, followed by straight-polarity electron beam irradiation.

15. The method of manufacturing the medical device according to claim 14, wherein the straight-polarity electron beam irradiation is performed at least twice under different voltage conditions.

16. The method of manufacturing the medical device according to claim 8, further comprising coating the outer surface which has been subjected to the electron beam irradiation with a film composed of a substance that is different from the titanium base material and the titanium alloy base material.

17. The method of manufacturing the medical device according to claim 16, wherein the substance that is different from the base material is diamond-like carbon.

18. The method of manufacturing the medical device according to claim 8, wherein the medical device is a blood pump device.

19. The method of manufacturing the medical device according to claim 15, wherein the blood pump device is a centrifugal blood pump device including dynamic pressure grooves.

\* \* \* \* \*